United States Patent
Zenker et al.

(10) Patent No.: US 7,345,004 B2
(45) Date of Patent: Mar. 18, 2008

(54) SCRIM REINFORCED ABSORBENT ARTICLE WITH REDUCED STIFFNESS

(75) Inventors: David L. Zenker, Neenah, WI (US); James Martin Kaun, Neenah, WI (US); Michael Barth Venturino, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 110 days.

(21) Appl. No.: 10/620,227

(22) Filed: Jul. 15, 2003

(65) Prior Publication Data

US 2005/0014428 A1    Jan. 20, 2005

(51) Int. Cl.
*D03D 9/00* (2006.01)
*D04H 1/00* (2006.01)
*D04H 3/00* (2006.01)
*D04H 5/02* (2006.01)
*B32B 5/26* (2006.01)

(52) U.S. Cl. .................. 442/36; 442/1; 442/2; 442/13; 442/14; 442/35; 442/50; 442/57

(58) Field of Classification Search ................. 442/1, 442/5, 2, 13, 14, 35, 36, 50, 57
See application file for complete search history.

(56) References Cited

U.S. PATENT DOCUMENTS

| | | | |
|---|---|---|---|
| 2,161,539 A * | 6/1939 | Swartz | 139/383 R |
| 2,964,039 A | 12/1960 | Johnson, Jr. et al. | |
| 3,085,309 A | 4/1963 | Olson | |
| 3,156,751 A | 11/1964 | Valdes et al. | |
| 3,587,579 A * | 6/1971 | Sabee | 604/365 |
| 3,629,047 A | 12/1971 | Davison | |
| 3,683,921 A | 8/1972 | Brooks et al. | |
| 3,768,479 A | 10/1973 | Widlund | |
| 3,816,231 A | 6/1974 | Marshall | |

(Continued)

FOREIGN PATENT DOCUMENTS

AU          458424     *   5/1973

(Continued)

OTHER PUBLICATIONS

International Search Report for PCT/US2004/006915 dated Nov. 5, 2004, 7 pages.

(Continued)

*Primary Examiner*—Terrel Morris
*Assistant Examiner*—Matthew D Matzek
(74) *Attorney, Agent, or Firm*—Armstrong Teasdale, LLP

(57) ABSTRACT

An absorbent structure can include a matrix of fibers, wherein the matrix is reinforced with a reinforcing member, such as scrim. The scrim is secured to the fibrous matrix by entanglement of fibers with the scrim and entanglement of fibers in the matrix from opposite sides of the scrim with each other. The scrim layer can be restricted to a longitudinally extending, medial region of the absorbent. In a particular arrangement, the scrim has a cross-directional width dimension which is less than a narrowest width dimension of the fibrous matrix. The scrim can be located between two, opposed, major surfaces of the fibrous matrix. The scrim has a reduced stiffness in the cross direction which promotes fit and comfort of the absorbent structure as incorporated into a disposable absorbent garment.

25 Claims, 9 Drawing Sheets

U.S. PATENT DOCUMENTS

| | | | |
|---|---|---|---|
| 3,856,012 A | 12/1974 | MacDonald et al. | |
| 3,862,877 A | 1/1975 | Camden | |
| 3,867,935 A | 2/1975 | Eisdorfer et al. | |
| 3,888,248 A | 6/1975 | Moore et al. | |
| 3,935,979 A | 2/1976 | Hickey | |
| 4,001,472 A | 1/1977 | Thomas et al. | |
| 4,028,455 A | 6/1977 | Ueda et al. | |
| 4,107,371 A * | 8/1978 | Dean | 442/3 |
| 4,141,772 A | 2/1979 | Buell | |
| 4,217,078 A | 8/1980 | Buell | |
| 4,235,237 A * | 11/1980 | Mesek et al. | 604/368 |
| 4,300,562 A | 11/1981 | Pieniak | |
| 4,303,189 A | 12/1981 | Wiley et al. | |
| 4,392,862 A | 7/1983 | Marsan et al. | |
| 4,425,127 A | 1/1984 | Suzuki et al. | |
| 4,606,964 A | 8/1986 | Wideman | |
| 4,639,253 A | 1/1987 | Dyer | |
| 4,640,810 A | 2/1987 | Laursen et al. | |
| 4,645,499 A | 2/1987 | Rupinskas | |
| 4,666,647 A | 5/1987 | Enloe et al. | |
| 4,674,966 A | 6/1987 | Johnson et al. | |
| 4,704,112 A | 11/1987 | Suzuki et al. | |
| 4,710,185 A | 12/1987 | Sneyd, Jr. et al. | |
| 4,761,258 A | 8/1988 | Enloe | |
| 4,764,325 A | 8/1988 | Angstadt | |
| 4,765,780 A | 8/1988 | Angstadt | |
| 4,773,903 A | 9/1988 | Weisman et al. | |
| 4,775,579 A | 10/1988 | Hagy et al. | |
| 4,810,568 A | 3/1989 | Buyofsky et al. | |
| 4,834,735 A | 5/1989 | Alemany et al. | |
| 4,837,715 A | 6/1989 | Ungpiyakul et al. | |
| 4,904,440 A | 2/1990 | Angstadt | |
| 4,908,175 A | 3/1990 | Angstadt | |
| 4,915,897 A | 4/1990 | Farrington et al. | |
| 4,915,993 A | 4/1990 | Ten Wolde | |
| 4,927,346 A | 5/1990 | Kaiser et al. | |
| 4,927,582 A | 5/1990 | Bryson | |
| 5,004,579 A | 4/1991 | Wislinski et al. | |
| 5,017,324 A | 5/1991 | Kaiser et al. | |
| 5,124,188 A | 6/1992 | Roe et al. | |
| 5,128,082 A | 7/1992 | Makoui | |
| 5,139,841 A | 8/1992 | Makoui et al. | |
| 5,144,729 A | 9/1992 | Austin et al. | |
| 5,161,283 A | 11/1992 | Hansen | |
| 5,219,633 A | 6/1993 | Sabee | |
| 5,281,208 A | 1/1994 | Thompson et al. | |
| 5,302,445 A | 4/1994 | DePetris et al. | |
| 5,328,072 A | 7/1994 | Ruessmann et al. | |
| 5,334,446 A * | 8/1994 | Quantrille et al. | 442/35 |
| 5,389,095 A | 2/1995 | Suzuki et al. | |
| 5,389,202 A | 2/1995 | Everhart et al. | |
| 5,429,788 A | 7/1995 | Ribble et al. | |
| 5,447,677 A | 9/1995 | Griffoul et al. | |
| 5,466,409 A | 11/1995 | Partridge et al. | |
| 5,486,167 A | 1/1996 | Dragoo et al. | |
| 5,505,720 A | 4/1996 | Walters et al. | |
| 5,514,120 A | 5/1996 | Johnston et al. | |
| 5,527,300 A | 6/1996 | Sauer | |
| 5,531,729 A | 7/1996 | Coles et al. | |
| 5,591,148 A | 1/1997 | McFall et al. | |
| 5,607,415 A | 3/1997 | Datta et al. | |
| 5,614,283 A | 3/1997 | Potnis et al. | |
| 5,622,581 A * | 4/1997 | Ducker et al. | 156/163 |
| 5,672,306 A | 9/1997 | Sprang et al. | |
| 5,704,931 A | 1/1998 | Holtman et al. | |
| 5,756,039 A | 5/1998 | McFall et al. | |
| 5,762,844 A | 6/1998 | Van Himbergen et al. | |
| 5,772,813 A | 6/1998 | Bitowft et al. | |
| 5,803,334 A | 9/1998 | Patel et al. | |
| 5,818,719 A | 10/1998 | Brandon et al. | |
| 5,871,613 A | 2/1999 | Bost et al. | |
| 5,873,963 A | 2/1999 | Trombetta et al. | |
| 5,902,757 A | 5/1999 | Stern et al. | |
| 5,916,661 A | 6/1999 | Benson et al. | |
| 5,925,439 A | 7/1999 | Haubach | |
| 5,938,648 A | 8/1999 | LaVon et al. | |
| 5,944,706 A | 8/1999 | Palumbo et al. | |
| 5,947,945 A | 9/1999 | Cree et al. | |
| 5,961,509 A | 10/1999 | Kling | |
| 5,997,520 A | 12/1999 | Ahr et al. | |
| 6,048,489 A | 4/2000 | Reiter et al. | |
| 6,060,637 A | 5/2000 | Bitowft et al. | |
| 6,090,994 A | 7/2000 | Chen | |
| 6,093,663 A * | 7/2000 | Ouellette et al. | 442/5 |
| 6,107,538 A | 8/2000 | Young et al. | |
| 6,203,654 B1 | 3/2001 | McFall et al. | |
| 6,204,207 B1 * | 3/2001 | Cederblad et al. | 442/5 |
| 6,258,996 B1 | 7/2001 | Goldman | |
| 6,262,331 B1 | 7/2001 | Nakahata et al. | |
| 6,284,943 B1 | 9/2001 | Osborn, III et al. | |
| 6,296,862 B1 | 10/2001 | Paul et al. | |
| 6,330,735 B1 | 12/2001 | Hahn et al. | |
| 6,375,644 B2 | 4/2002 | Mizutani | |
| 6,416,697 B1 | 7/2002 | Venturino et al. | |
| 6,492,574 B1 | 12/2002 | Chen et al. | |
| 6,533,978 B1 | 3/2003 | Wisneski et al. | |
| 6,533,989 B1 | 3/2003 | Wisneski et al. | |
| 6,575,948 B1 | 6/2003 | Kashiwagi et al. | |
| 6,630,096 B2 | 10/2003 | Venturino et al. | |
| 6,802,834 B2 * | 10/2004 | Melius et al. | 604/385.31 |
| 2001/0027305 A1 | 10/2001 | Raidel et al. | |
| 2001/0039405 A1 | 11/2001 | Keuhn, Jr. et al. | |
| 2002/0009940 A1 * | 1/2002 | May et al. | 442/328 |
| 2003/0116888 A1 | 6/2003 | Rymer et al. | |
| 2003/0119401 A1 | 6/2003 | Chakravarty et al. | |
| 2003/0132556 A1 | 7/2003 | Venturio et al. | |
| 2003/0139721 A1 | 7/2003 | Melius et al. | |
| 2003/0171728 A1 | 9/2003 | Heyn et al. | |
| 2004/0061263 A1 | 4/2004 | Daniels et al. | |
| 2004/0061264 A1 | 4/2004 | Heyn et al. | |
| 2004/0092898 A1 * | 5/2004 | Schafer et al. | 604/367 |
| 2004/0098838 A1 | 5/2004 | Venturino et al. | |
| 2004/0102751 A1 | 5/2004 | Schueler, Jr. | |
| 2004/0102752 A1 | 5/2004 | Chen et al. | |

FOREIGN PATENT DOCUMENTS

| | | |
|---|---|---|
| AU | 458424 | 2/1975 |
| DE | 198 23 954 A1 | 12/1999 |
| EP | 0 151 018 A2 | 8/1985 |
| EP | 0 226 939 A2 | 7/1987 |
| EP | 0 298 348 A1 | 1/1989 |
| EP | 0 399 511 A2 | 11/1990 |
| EP | 0 467 409 A1 | 1/1992 |
| EP | 0 297 180 B1 | 3/1992 |
| GB | 2 168 612 A | 6/1986 |
| JP | 09122172 | 5/1997 |
| JP | 10211236 | 8/1998 |
| WO | WO 93/18729 A1 | 9/1993 |
| WO | WO 95/34264 * | 12/1995 |
| WO | WO 96/00550 A1 | 1/1996 |
| WO | WO 98/22064 A1 | 5/1998 |
| WO | WO 99/22685 A1 | 5/1999 |
| WO | WO 99/25281 A1 | 5/1999 |
| WO | WO 00/10498 A1 | 3/2000 |
| WO | WO 00/37000 A1 | 6/2000 |
| WO | WO 00/37725 A1 | 6/2000 |
| WO | WO 0037000 * | 6/2000 |
| WO | WO 00/56257 A1 | 9/2000 |
| WO | WO 00/63479 A1 | 10/2000 |
| WO | WO 01/92003 A1 | 12/2001 |

WO  WO 03/059232 A2  7/2003

OTHER PUBLICATIONS

International Search Report for PCT/US 03/01337 dated Jul. 21, 2003.
International Search Report for PCT/US03/15959 dated Feb. 3, 2004.
International Search Report for PCT/US03/16480 dated Oct. 13, 2003.
International Search Report for PCT/US2004/008428 dated Aug. 23, 2004, 4 pages.
International Search Report for PCT/US 03/00293 dated Jul. 29, 2003.

* cited by examiner

SCRIM REINFORCED ABSORBENT ARTICLE WITH REDUCED STIFFNESS

BACKGROUND OF THE INVENTION

1. Field of the Invention

This invention relates generally to an absorbent article, and more particularly to improvements in scrim reinforced absorbent cores having reduced stiffness. The reinforced absorbent structure can be employed in absorbent articles, such as disposable diapers, child's training pants, feminine care articles, incontinence articles, bandages, and the like.

2. Description of the Prior Art

Absorbent articles typically include fluid absorbent structures or cores conventionally formed by air forming or air laying techniques, and are placed between an intake function liner and a barrier function liner. The manufacture of the absorbent core may begin by fiberizing a sheet of cellulosic or other suitable absorbent material in a conventional fiberizer, or other shredding device, to form discrete fibers, and particles of superabsorbent material may be mixed with the discrete fibers. The fibers and superabsorbent particles are then entrained in an air stream and directed to and deposited on a foraminous forming surface to form an absorbent fibrous web. In addition, bonding agents or other strengthening components may be incorporated to provide a more stabilized web.

Other techniques have also been employed to form webs of stabilized absorbent material. Such techniques have included dry-forming techniques, foam-forming techniques, and various wet-laying and wet-forming techniques. The resulting webs of absorbent material have included absorbent fibers, natural fibers, synthetic fibers, superabsorbent materials, binders, and strengthening components in desired combinations. However formed, the absorbent web is then processed (e.g., cut into individual article cores) and assembled with other components (intake and barrier layers) to produce a final absorbent article. Absorbent material webs have also been strengthened by adding reinforcing members to the absorbent material webs. Such reinforcing members have included reinforcement filaments, tissue layers, fabric layers and netting materials. It is also known to add staple binder fibers to the absorbent materials upon formation of the absorbent material web. The binder fibers are activated by heat to produce adhesion of the absorbent materials.

Integrity of an absorbent core formed from such an absorbent material web is desirable to avoid bunching, clumping, cracking and separating of the absorbent core in either a wet or a dry state so as to improve the fit and comfort to the wearer of the absorbent article. Sagging and drooping of the absorbent article due to fluid insults can cause gaps between the article and the wearer's body which may lead to leaking, and poor integrity resulting in absorbent cracking and separating in use continues to be a common problem with conventional airformed absorbent cores.

As absorbent cores are made both thinner and narrower to achieve increased comfort (particularly in the crotch region), web stresses encountered in manufacture and use can be high, requiring better reinforcement. For instance, in manufacture tension on the absorbent core can be particularly high during start up and shut down of processing machinery. In use, the lack of integrity can make the absorbent article fit poorly and impact product performance through the cracking or breaking up of the absorbent core, and thereby inhibiting fluid control, liquid handling and wicking which can contribute to leaking.

Co-assigned European Patent Publication No. 0 467 409 A1 discloses one attempt to reinforce an absorbent pad using a scrim material. In that disclosure, a netting of scrim material is used in which some strands have an inner core of one material and an outer sheath of a second material having a lower melting point. The scrim is incorporated into a fibrous matrix, and this absorbent web is heated to melt the outer sheath for bonding the scrim to the matrix fibers. This requires an extra step in the manufacture of a reinforced absorbent.

European Publication No. 0 467 409 also discloses a method for establishing the position of the scrim within the body thickness of fibrous matrix. The method does not require a scrim of different materials, or suggest that the scrim can be secured without the use of adhesive and/or fusion bonding.

The incorporation of a scrim reinforcement material internally into the structure of the absorbent core dramatically reduces this integrity problem. However, in some cases certain scrim reinforcement can also result in undesirable absorbent stiffness which adversely impacts conformability, fit and comfort, especially in the crotch region of the absorbent article. The marginal edges of the scrim may cause skin irritation. These problems are particularly relevant for a narrow crotch geometry, where the buckling span is shorter as compared to wide crotch executions.

As a result, it has been difficult to achieve an absorbent structure having the desired features of low-cost, high strength and low irritation in addition to the basic attributes of comfort and high fluid absorption.

SUMMARY OF THE INVENTION

The invention is embodied in an absorbent article having an absorbent core including a reinforcement scrim member for providing good structural integrity when wetted during use, the scrim member being constructed and arranged with a plurality of elongate, integral machine direction (MD) strands and a plurality of cross direction (CD) strands forming a scrim network having an increased edge load yieldability in the direction of the CD strands. In one aspect, the reinforcing member can be restricted to a longitudinally extending, medial region of the absorbent structure and the reinforcing member can have a cross-directional width dimension which is less than a narrowest width dimension of the absorbent core. In a further aspect, the reinforcing member material can be located at any desired level in the thickness (TD) of the absorbent core.

In one embodiment of the invention, an absorbent article has a reinforcing member formed of crossed CD and MD strands constructed and arranged with characteristic differences to provide reduced stiffness in the CD direction.

In a further aspect, an absorbent article includes a reinforcing scrim member for maintaining the structural integrity of the absorbent core member, which scrim member has plural MD strands and crossing CD strands having a reduced frequency.

In a further aspect, an absorbent article includes a reinforcing scrim member for maintaining the structural integrity of the absorbent core member, which scrim member has plural MD strands and crossing CD strands having a reduced thickness.

In a further aspect, an absorbent article includes a reinforcing scrim member for maintaining the structural integrity of the absorbent core member, which scrim member has plural MD strands and crossing CD strands extending in non-perpendicular direction to the MD strands.

In a further aspect, an absorbent article includes a reinforcing scrim member for maintaining the structural integrity of the absorbent core member, which scrim member has plural MD strands and crossing CD strands selectively weakened by cutting, notching or deforming.

In a still further aspect, an absorbent article includes a reinforcing scrim member for maintaining the structural integrity of the absorbent core member, which scrim member has plural MD strands extending generally in an x-direction, the CD strands extending in a y-direction and having a lower modulus of elasticity raw material than the MD strands.

In a further aspect, an absorbent article includes a reinforcing scrim member for maintaining the structural integrity of the absorbent core member, which scrim member has plural MD strands and crossing CD strands that are relatively softer, flexible or yieldable.

In a still further aspect, the absorbent article includes a core reinforcement scrim member having optimum strength in the MD direction and reduced CD strand stiffness while supporting MD strand spacing and function.

Other features, objects and advantages of the invention will become more apparent hereinafter.

BRIEF DESCRIPTION OF THE DRAWINGS

Corresponding reference characters indicate corresponding parts throughout the several views of the drawings.

DETAILED DESCRIPTION OF THE DRAWINGS

The disclosure of co-assigned and co-pending patent application Ser. No. 10/306,086 filed Nov. 27, 2002 for Absorbent Article With Reinforced Absorbent Structure is incorporated herein by reference for the purpose of showing the various absorbent article constructions and materials that may be associated in forming certain commercial embodiments.

The technology of the invention can be configured to produce various types of desired absorbent articles. Such articles can include, for example, infant diapers, children's training pants, feminine care articles, adult incontinence garments, bandages and the like for use in absorbing various body exudates. The articles may be, but are not necessarily, disposable, and intended for limited use.

Figure 1:
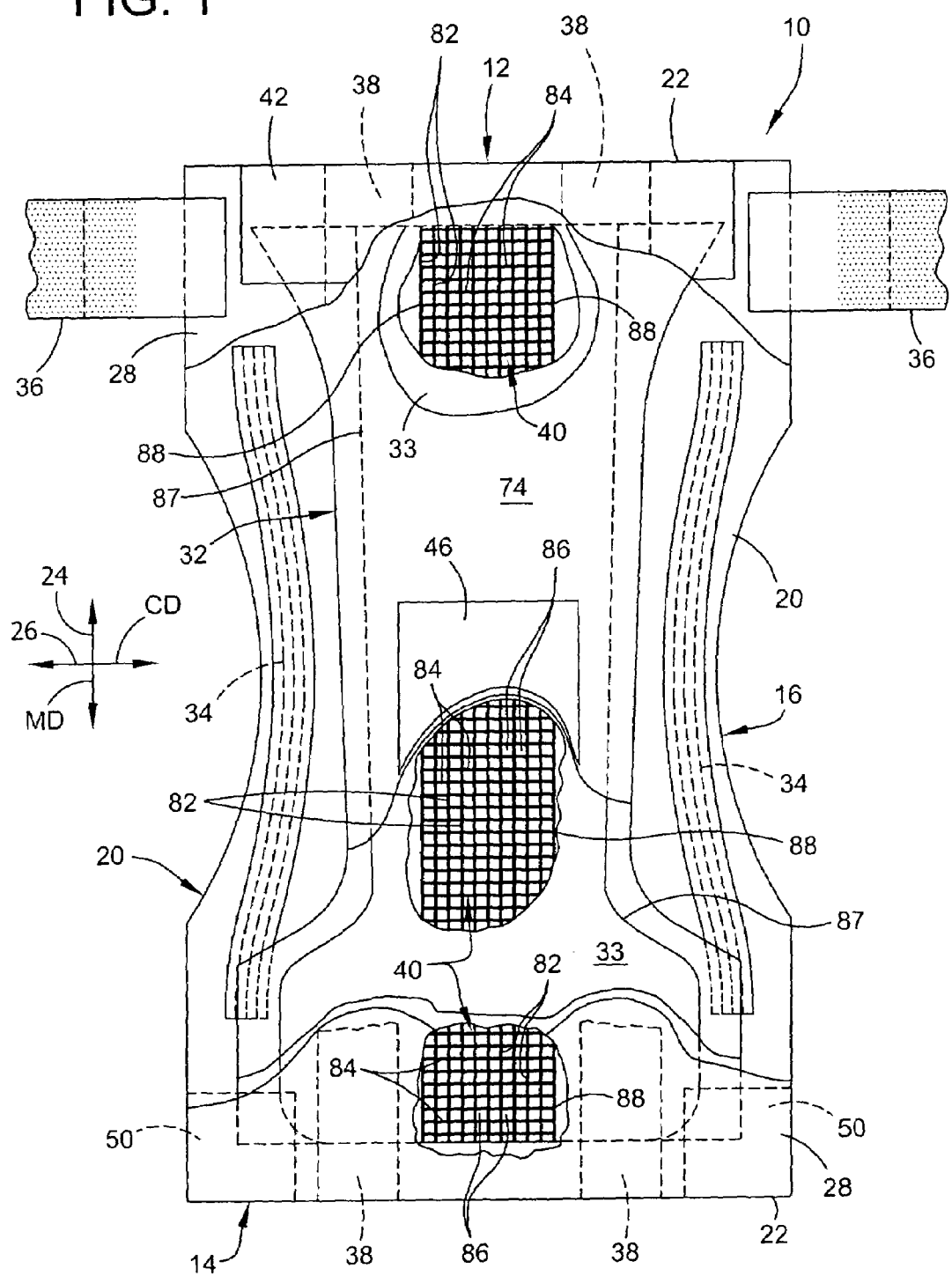
FIG. 1 is a top plan view of a representative absorbent article, partly broken away to show internal construction.

Referring now to the drawings, and in particular to FIGS. 1 and 2, for disclosure purposes an absorbent article constructed according to the principles of the present invention is shown in the form of a diaper 10 unfolded and laid flat with substantially all elastic induced gathering and contraction areas removed. The diaper 10 extends lengthwise in a longitudinal or machine-direction 24 (MD), widthwise in a lateral or cross-direction 26 (CD), and has a depth or thickness in a thickness direction 25 (TD) (see FIG. 3). For purposes of the present disclosure, the machine-direction 24 (called "MD") lies parallel to the plane of the diaper 10, and extends generally between opposed end regions (12, 14) of the diaper. The cross-direction 26 (called "CD") also lies parallel to the plane of the article, and is generally transversely oriented or perpendicular relative to the longitudinal MD strand direction 24. The thickness direction 25 (called "TD") is oriented substantially perpendicular or normal to the plane of both the elongate MD direction 24 and the transverse CD direction 26, and extends through the thickness of the diaper 10. In FIG. 1, the bodyside surface of the diaper which contacts the wearer faces upwardly and portions of the structure are partially cut away to more clearly show the interior construction of the diaper article 10. The outer edges of the diaper define a periphery with longitudinally extending side edge margins 20 and laterally extending end edge margins 22. The side edges 20 will define leg openings for the diaper 10, in use.

With regard to the designated surfaces of the article, the various inward or bodyside surfaces are configured to face against the body of the wearer when the article is placed in use. The designated outward surfaces of the article are configured to face away from the wearer's body when the article is placed in use. The diaper 10 may have any desired shape, such as rectangular, I-shaped, a generally hourglass shape, or a T-shape.

The diaper 10 includes an absorbent inner structure, generally indicated at 32, having an absorbent core 33 (broadly, "an absorbent member") which may include both absorbent fibers and superabsorbent material (SAM) to be described. The absorbent core 33 may also include other fibers which are not absorbent. A web of scrim 40 (broadly, "a reinforcing member") is located roughly in the middle of the absorbent core 33 (FIG. 2A) for reinforcing the fibrous absorbent core to enhance the integrity of the core during use as will be described more fully hereinafter. The actual thickness direction 25 orientation of the scrim 40 between major surfaces of the core 33 may vary in applications where the core has a non-constant thickness. It is also to be understood that the scrim can be placed away from the middle, toward one side surface (FIG. 2B) or the other side surface (FIG. 2C) within the absorbent core and still come within the scope of the invention. A backsheet barrier layer 30 and a liquid permeable topsheet or intake layer 28 are arranged on opposite sides from each other and the absorbent structure 32 is located between these layers. Typically, the backsheet layer 30 is liquid impermeable, but may be liquid permeable for some applications without departing from the scope of the present invention. The illustrated diaper 10 has a first or back waistband portion 12, a second or front waistband portion 14 and an intermediate or crotch portion 16 that interconnects the back and front waistband portions. In use, the diaper 10 is fitted onto the lower torso and around the upper legs of a wearer (e.g., a child or infant), assuming a curved and three dimensional configuration in which parts of the back and front waistbands portions 12, 14 are overlapped or lie in close proximity to each other.

It will be understood that different absorbent articles to which the invention applies may require different features or combinations and arrangements of parts. The absorbent article selected for disclosure is a child's diaper 10, and a brief discussion of certain diaper features is believed to be relevant including diaper fastening systems and elastomeric gathering members, as now described.

A diaper fastening system includes a first fastener component in the form of fastener tabs 36 on the back waist band portion 12 and a second fastener component in the form of landing zone patches 50 on the front waistband portion 14 to hold the article in place on a wearer so that the back portion overlaps the front portion. The landing zone patches 50 provide a target area for releasable and re-attachable securement with the fastener tabs 36. The landing zone patches 50 are positioned on the outward surface of the backsheet layer 30. It is understood that an alternate fastening arrangement (not shown) could be used in which a front waistband portion overlaps the back waistband portion, whereby the front waistband portion would be the "first" waistband portion and the back waistband region would be the "second" waistband portion. One or more alternative fastener tabs and landing patch members can be selectively placed on the first or second waistband portions. The landing zone patches 50 and the fastener tabs 36 can be made of a substantially non-elastomeric material, such as polymer films or tapes, woven or non-woven fabrics, or the like. The landing zone patch 50 could also be made of a substantially elastomeric material, such as a stretch-bonded-laminate (SBL) material, an elastomeric neck-bonded-laminate (NBL) material, an elastomeric film an elastomeric foam material, or the like which is elastomerically stretchable.

In a broad context the aforesaid fastening mechanism between the selected first and second fastener components may be adhesive, cohesive, mechanical or combinations thereof. Desirably, the first and second fastener components include complementary elements of cooperatively interengaging mechanical-type fasteners such as hooks, buckles, snaps, buttons and the like. As shown, a suitable mechanical fastening system is of the hook-and-loop type. Such fastening systems typically include a first attachment member in the form of a "hook" or hook-like, male component, and a second member in the form of a cooperating "loop" or loop-like, female component that is engaged and releasably interconnected with the first hook component. Such conventional systems are, for example, available under the VELCRO trademark, and the hook element may have a single-prong hook configuration, a multiple-prong hook configuration or a generally continuous, expanded-head configuration, such as provided by a mushroom-head type of hook element. The loop element may be a woven, nonwoven or knitted fabric, or a perforated or apertured layer, as well as combinations thereof.

The diaper typically also has a system of elastomeric gathering members, including leg elastics 34 to hold the diaper 10 closely around the legs and a waist elastic 42 (located in the back waistband portion 12) to draw the diaper around the waist. In addition, elasticized containment flaps 38 may be provided to extend generally lengthwise in the machine-direction 24 of the diaper 10. The containment flaps 38 are typically positioned laterally inboard from the leg elastics 34, and substantially symmetrically placed on each side of the longitudinal centerline of the diaper to closely contact and conform to the contours of the wearer's body. Examples of suitable containment flap constructions are described in U.S. Pat. No. 4,704,116 entitled DIAPERS WITH ELASTICIZED SIDE POCKETS issued Nov. 3, 1987, and U.S. Pat. No. 5,562,650 entitled ABSORBENT ARTICLE HAVING AN IMPROVED SURGE MANAGEMENT issued Feb. 13, 1996. Alternative configurations may include internal, elasticized, containment waist flaps, such as those described in U.S. Pat. No. 4,753,646 entitled DIAPER WITH WAIST FLAPS issued Jun. 28, 1988; and in U.S. Pat. No. 5,904,675 entitled AN ABSORBENT ARTICLE WITH IMPROVED ELASTIC MARGINS AND CONTAINMENT SYSTEM issued May 18, 1999. Such containment waist flaps may be composed of a wettable or non-wettable material, as desired, and the waist flap material may be substantially liquid-impermeable, permeable to only gas, or permeable to both gas and liquid.

The diaper 10 can also include a surge management member 46 which helps to decelerate and diffuse surges or gushes of liquid that may be rapidly introduced into the absorbent structure of the article. Desirably, the surge management member 46 can rapidly accept and temporarily hold the liquid prior to releasing or wicking the liquid into the main absorbent core structure 32. In the illustrated FIG. 1 embodiment, for example, the surge member 46 is located on an interiorly facing side of the topsheet layer 28 so as to be interposed between the topsheet layer and the absorbent core structure 32. Examples of suitable surge management members 46 are described in U.S. Pat. No. 5,486,166 issued Jan. 23, 1996 entitled FIBROUS NONWOVEN WEB SURGE LAYER FOR PERSONAL CARE ABSORBENT ARTICLES AND THE LIKE; and U.S. Pat. No. 5,490,846 issued Feb. 13, 1996 entitled IMPROVED SURGE MANAGEMENT FIBROUS NONWOVEN WEB FOR PERSONAL CARE ABSORBENT ARTICLES AND THE LIKE.

As indicated, the barrier or backsheet layer 30 is located along an outside surface of the absorbent structure 32 (away from the wearer) and desirably comprises a substantially liquid impermeable material, such as a thin plastic film, or other relatively soft and flexible material. As used herein, the term "flexible" refers to materials which are compliant and which will readily conform to the general shape and contours of the wearer's body. The primary function of the backsheet layer 30 is to contain or hold the exudates absorbed into the absorbent core structure 32 and prevent the soiling of outside articles which contact the diaper 10, such as bedsheets and overgarments. In a particular embodiment of the invention, the backsheet layer 30 can include a film, such as a polyethylene film, having a thickness of from about 0.012 millimeters (0.5 mil) to about 0.051 millimeters (2.0 mil). For example, the backsheet film can have a thickness of about 0.032 millimeters (1.25 mil). Alternative constructions of the backsheet layer 30 may comprise a woven or non-woven fibrous web that is totally or partially constructed or treated to impart the desired levels of liquid impermeability to selected regions that are adjacent or proximate the absorbent structure. Specific examples of acceptable alternate backsheet or barrier materials are disclosed in co-assigned patent application Ser. No. 10/306,086 (previously cited and herein incorporated by reference).

As also indicated, the topsheet layer 28 presents a body-facing surface that is compliant, soft-feeling, and non-irritating to the wearer's skin. Further, the material of the topsheet intake layer 28 is more hydrophobic than the absorbent structure 32, but is sufficiently porous to be liquid permeable, thus permitting fluids to readily pass through its surface ply thickness to reach the absorbent core structure 33. A suitable topsheet layer 28 may be manufactured from a wide selection of materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in the absorbent core structure 32. Specific examples of acceptable alternate topsheet or intake layer materials are disclosed in co-assigned patent application Ser. No. 10/306,086 (previously cited and incorporated herein by reference).

The absorbent structure 32 has a construction that is generally compressible, conformable, non-irritating to the wearer's skin, and capable of absorbing and retaining body exudates. It should be understood that, for purposes of this invention, the absorbent structure 32 comprises several parts that are assembled together. The absorbent core 33 of the absorbent structure 32 may be constructed of any of a number of absorbent materials, as are well known in the art. For example, the absorbent core 33 may be provided by a layer of coform, meltblown fibers, bonded carded webs, a wetlaid body, tissue laminates, foams, a surge/air formed composite and the like or combinations thereof. In particular, the absorbent core 33 may be provided as a combination of hydrophilic fibers, and high-absorbency material.

The absorbent core 33 may also be zoned to provide for additional retention of liquid (as compared to the other regions of the core 33). Descriptions of ways to form zoned absorbent cores are disclosed in co-assigned U.S. Pat. No. 4,761,258 entitled CONTROLLED FORMATION OF LIGHT AND HEAVY FLUFF ZONES issued Aug. 2, 1988; U.S. Pat. No. 6,330,735, entitled APPARATUS AND PROCESS FOR FORMING A LAID FIBROUS WEB WITH ENHANCED BASIS WEIGHT CAPABILITY issued Dec. 18, 2001; and U.S. patent application Ser. No. 10/207,929 entitled APPARATUS AND FORM FOR MAKING AN AIR FORMED FIBROUS WEB filed Jul. 30, 2002.

Various types of wettable, hydrophilic fibrous material can be used to provide the fiber material for the absorbent core 33. Examples of suitable fibers include naturally occurring organic fibers composed of intrinsically wettable material, such as cellulosic fibers including wood pulp fibers which can be curled, crosslinked or otherwise mechanically or chemically modified. Other examples of suitable fibers include synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with another material that has a suitable hydrophilic moiety and is not readily removable from the fiber, or by sheathing the nonwettable, hydrophobic fiber with a hydrophilic polymer during or after the formation of the fiber.

The high-absorbency material used in the absorbent core 33 may comprise absorbent gelling materials, such as superabsorbent materials. Absorbent gelling materials can be natural, biodegradable, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces. Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed in U.S. Pat. No. 3,901,236 issued Aug. 26, 1975 and processes for preparing synthetic absorbent gelling polymers are disclosed in U.S. Pat. No. 4,076,663 issued Feb. 28, 1978 and U.S. Pat. No. 4,286,082 issued Aug. 25, 1981. Superabsorbent materials are well known in the art, and are readily available from various suppliers. For example, FAVOR SXM 880 superabsorbent is available from Stockhausen, Inc., a business having offices located in Greensboro, N.C., U.S.A.; and DRYTECH 2035 is available from Dow Chemical Company, a business having offices located in Midland, Mich., U.S.A.

The high-absorbency material used in the absorbent core 33 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the absorbent core 33. Desired for use are particles having an average size of from about 20 micrometers to about 1 millimeter. "Particle size" as used herein means the weighted average of the smallest dimension of the individual particles.

The absorbent materials and superabsorbent materials may be integrated into the absorbent core by any of several known methods such as a dry-forming technique, an air forming technique, a wet-forming technique, a foam-forming technique or the like. One example is described more fully below in reference to FIG. 13.

The web of scrim 40 is incorporated into the absorbent core 33 of the absorbent structure 32. In a representative illustration in FIG. 3, the scrim 40 comprises elongate strands which are arranged in a grid including spaced parallel strands 82 (MD) extending in the machine-direction 24 and crossing strands 84 (CD) extending in the cross-direction 26 defining rectangular or like openings 86 in the scrim. Among other things, the openings 86 permit liquid in the absorbent core 33 to flow substantially unhindered through the scrim 40. The strands 82, 84 are secured to each other where they intersect to create a lattice providing strength and stability to the absorbent core. In one embodiment, the width of the scrim 40 is equal to the minimum width of the absorbent core 33 (usually located at the portion of the core which is worn through the crotch). In other embodiments, the width of the scrim 40 is between 25% and 100% and between 50% and 100% of the narrowest width dimension of the absorbent core 33.

The scrim 40 can be made of any suitable material that provides desired levels of strength and flexibility. For example, the strands 82, 84 of the scrim 40 may be composed of natural or synthetic materials, as well as combinations thereof. Synthetic materials may include a synthetic polymer (e.g., polyester, polyethylene, polypropylene, nylon, rayon). The synthetic polymer may be monofilament, bicomponent or multicomponent. One conventional way to form scrim of such material is to extrude and orient the MD and CD strands 82, 84 to form a net or mesh configuration. Natural materials that could be used to form the scrim include cotton, jute, hemp, and wool. The reinforcing scrim 40 can be a woven or nonwoven material. The scrim strands 82 in the machine-direction 24 could be of a different material than the strands 84 in the cross direction 26. Different materials could also be used as alternating scrim strands in the machine-direction and/or in the cross-direction, as will appear. In one embodiment, the strands 82, 84 may be formed of superabsorbent material. In that event, the scrim 40 would serve a liquid retention function in addition to its reinforcing function. Still further, the scrim 40 could be formed of one material and coated with another material, or be a biodegradable material, such as polylactic acid. An example of a superabsorbent coating is given in co-assigned application Ser. No. 10/246,811 entitled ABSORBENT ARTICLES HAVING A SUPERABSORBENT RETENTION WEB by Newbill et al., filed Sep. 18, 2002, the disclosure of which is incorporated herein by reference.

The scrim position in the thickness direction 25 within the absorbent core 32 is preselected. In FIG. 1 the scrim 40 is shown extending the full length of the absorbent core 33, but may have a lesser or greater length. The inner absorbent core 33 has longitudinal outer side edges 87. The scrim 40 is narrower than the absorbent core 33 and arranged so that its longitudinal side edges 88 are located inwardly of the longitudinal edges 87. In this way, longitudinal edges 88 of the scrim 40 are embedded in and shielded by the fibrous material of the absorbent core 33 so they do not irritate the skin or abrade or poke holes in other parts of the diaper 10. The core 33 is shown in FIG. 1, to extend lengthwise of the diaper and to embed the scrim 40. It has been found that the scrim 40 helps the absorbent core 33 hold its shape in conformance with the wearer's body thereby maintaining integrity of fit and comfort in both wet and dry conditions.

Figure 2A:
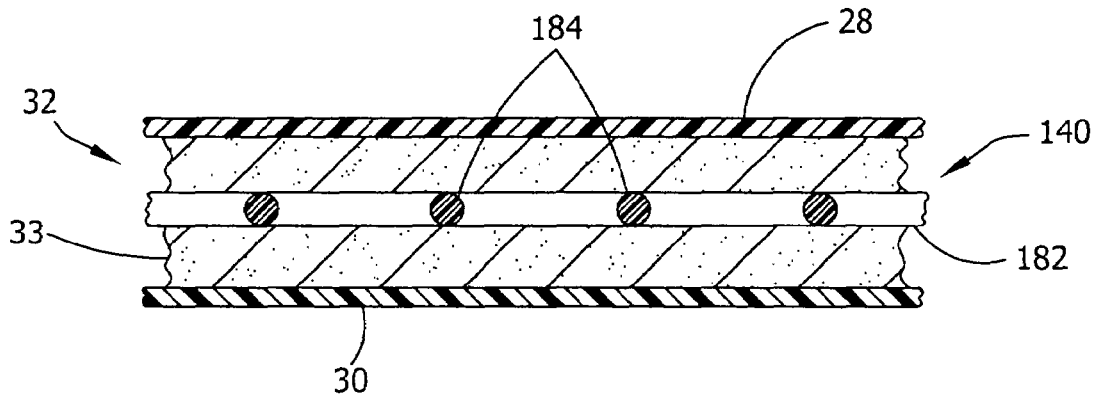
FIG. 2A is an enlarged, fragmentary cross-section of a typical absorbent core showing a placement therein of one embodiment of a reinforcement scrim member according to FIG. 4.
Figure 2B:
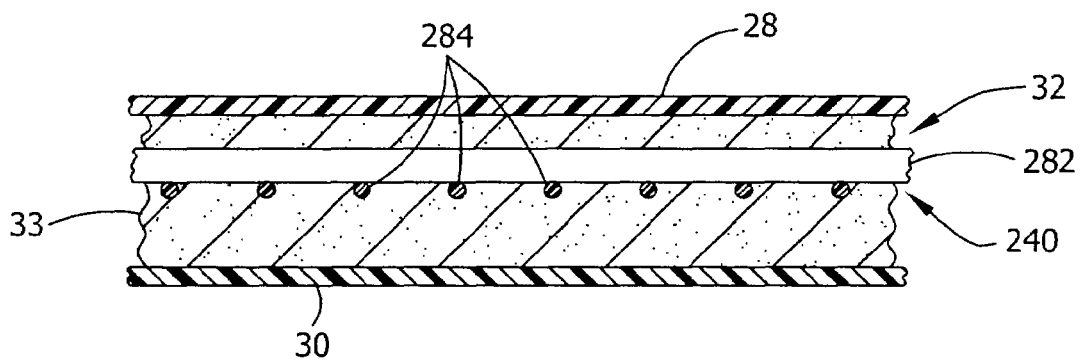
FIG. 2B is an enlarged, fragmentary view similar to FIG. 2A showing an alternate orientation in an absorbent core of a second reinforcing scrim member embodiment according to FIG. 5.
Figure 2C:
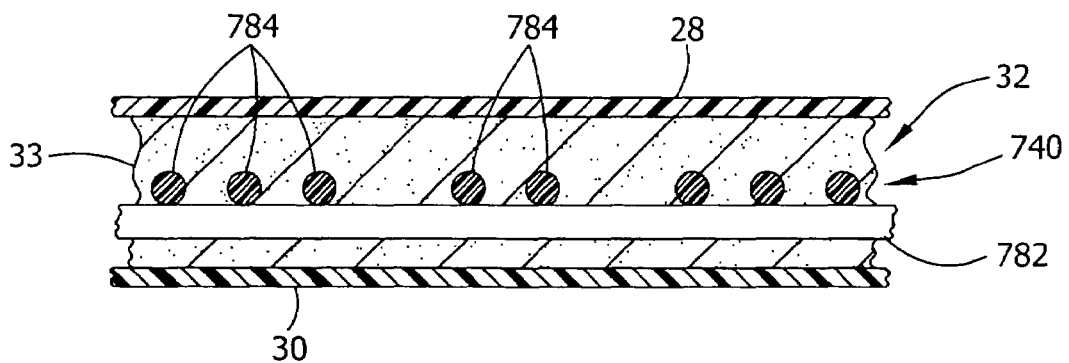
FIG. 2C is a view similar to FIGS. 2A and 2B showing a third alternate orientation in an absorbent core of a third reinforcement scrim member embodiment according to FIG. 10.
Figure 3:
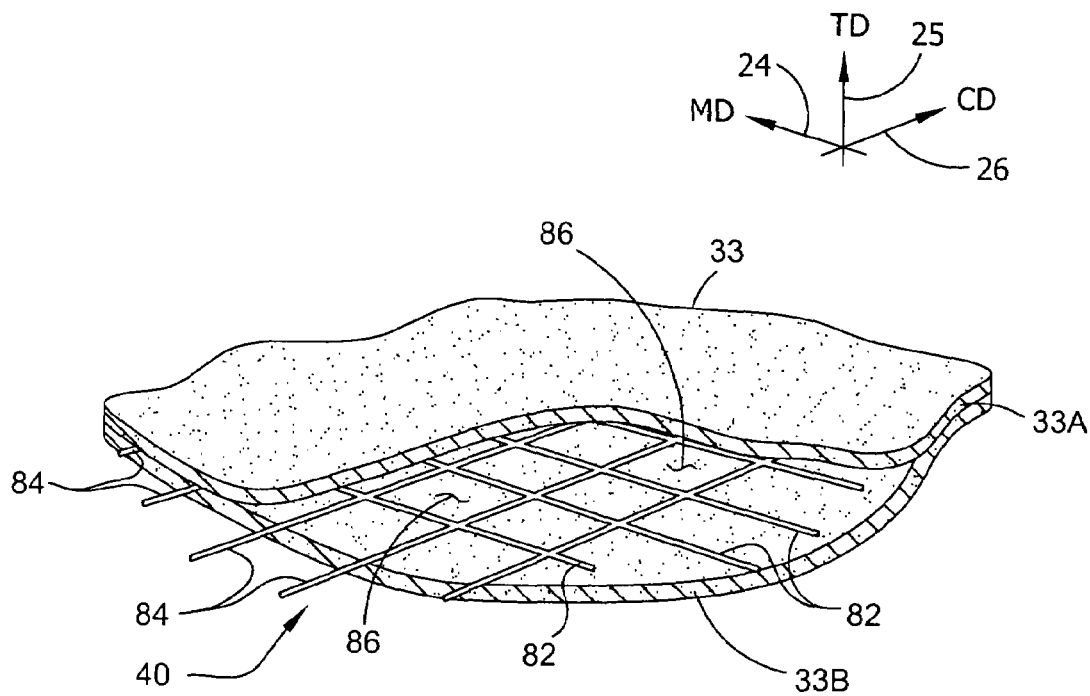
FIG. 3 is a greatly enlarged, fragmentary perspective view of an absorbent core to further illustrate the FIG. 2A embodiment.

The scrim 40 typically defines a substantially central or intermediate position in the TD direction 25 between upper and lower regions 33A and 33B of the absorbent core 33 (FIG. 2A). However, because the scrim 40 is narrower than the absorbent core 33, the upper and lower regions 33A, 33B have no dividing boundary plane and are not distinct away from the scrim. As previously indicated, FIGS. 2B and 2C illustrate alternate thickness direction (TD) placements of the scrim 40 within the absorbent core 33. The scrim 40 may be incorporated in the absorbent core 33 in a suitable manner, such as during the formation of the absorbent core. Suitable air forming methods and apparatus for such incorporation are disclosed in co-assigned U.S. patent application Ser. No. 10/306,269, entitled PROCESS AND APPARATUS FOR MAKING A REINFORCED FIBROUS ABSORBENT MEMBER, by Venturino et al. and Ser. No. 10/305,755, entitled PROCESS AND APPARATUS FOR AIR FORMING AN ARTICLE HAVING A PLURALITY OF REINFORCED SUPERIMPOSED FIBROUS LAYERS, by Heyn et al., and Ser. No. 10/306,186, entitled CONTROLLED PLACEMENT OF A REINFORCING WEB WITHIN A FIBROUS ABSORBENT by Venturino et al., filed simultaneously herewith, the disclosures of which are incorporated herein by reference. It is noted that these forming methods and apparatus promote the entanglement of the fibers with the scrim 40 and with each other during manufacture of the absorbent core 33. This mechanical connection between the upper region 33A and the lower region 33B, and between both of those regions and scrim 40, is discussed more fully in co-assigned U.S. patent application Ser. No. 10/306,086 (previously cited and incorporated by reference). At least some fibers from the upper region 33A pass through openings 86 in the scrim 40 and are entangled with fibers from the lower region 33B and, in the same way, at least some of the fibers from the lower region 33B pass through the openings 86 in the scrim 40 and are entangled with fibers in the upper region 33A whereby the upper and lower regions 33A and 33B are connected to each other by fiber entanglement through the scrim 40. In addition, at least some fibers from the upper and lower regions 33A and 33B may be entangled with the strands 82, 84 of the scrim 40 itself so there is a strong mechanical joining of the upper and lower regions 33A, 33B to each other and with the scrim 40. The absorbent structure does not require the use of an adhesive to bond the scrim 40 with the fibers of the core 33, and does not require fusion of the scrim with the fibers to produce a robust and durable absorbent core.

In use, the scrim 40 brings added integrity to the absorbent structure by holding the matrix of the fibrous material together against loads applied through movement of the wearer and by liquid insults. These loads tend to cause the fibrous material (and hence the absorbent core 33) to tear apart. The scrim 40 resists forces applied to the absorbent core 33 such as but not limited to tensile, compressive, and shear. The scrim 40 allows the absorbent core 33 to have a lower base weight of fibrous material because of the additional strength. Accordingly, the construction of a thinner absorbent core 33 and a thinner absorbent structure 32 is facilitated.

Figure 13:
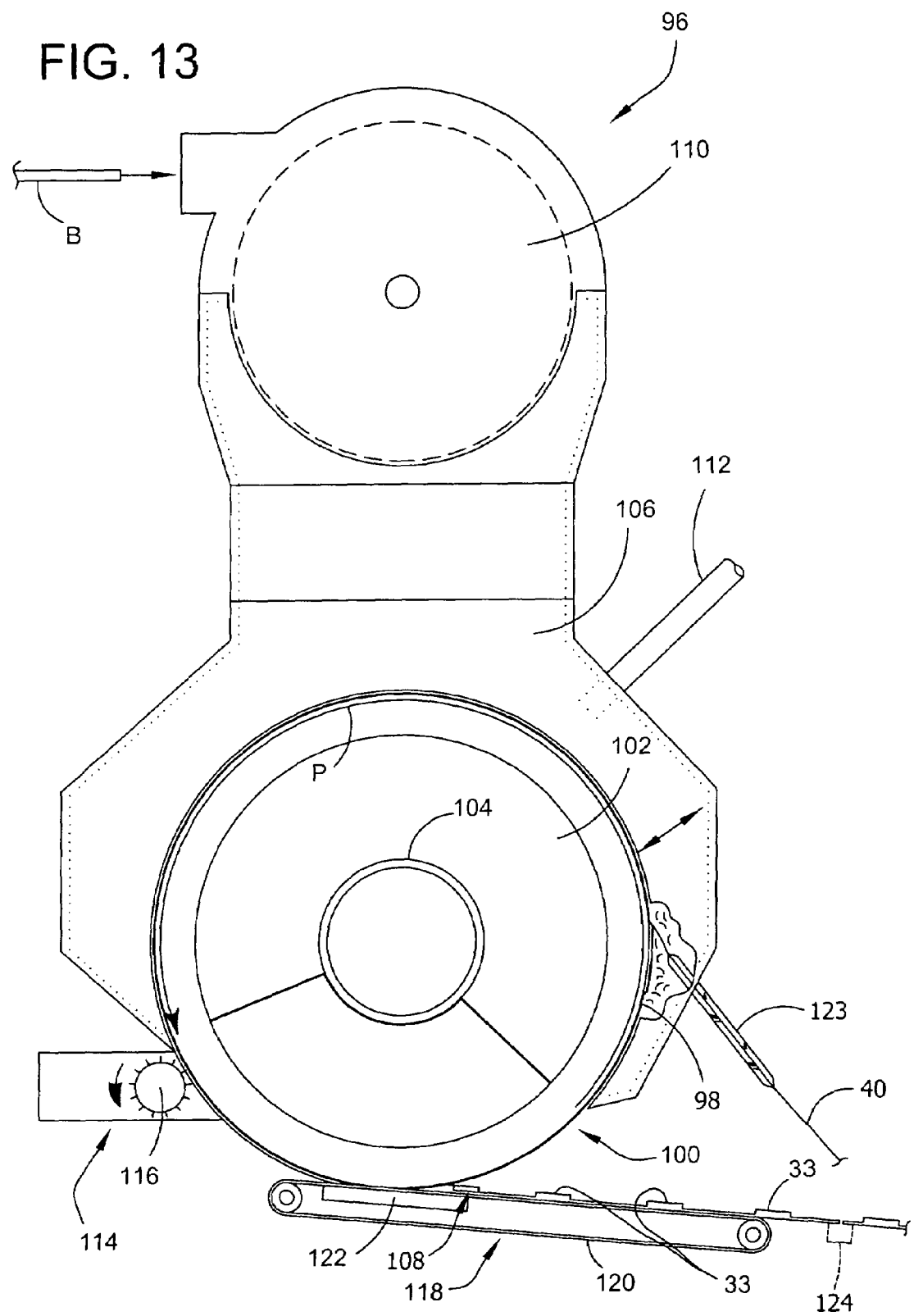
FIG. 13 is a diagrammatic elevational representation of an air forming apparatus to illustrate a manufacturing technique.

Absorbent cores 33 having reinforcing members 40 may be made using conventional air forming apparatus, such as the type indicated generally at 96 in FIG. 13 and discussed more fully in the aforesaid co-pending U.S. application Ser. No. 10/306,086 (incorporated by reference). The apparatus 96 comprises a movable, foraminous forming surface 98 extending about the circumference of a rotating drum 100. A vacuum duct 102 is arranged to draw a vacuum under the foraminous forming surface 98. The vacuum duct 102 is mounted in fluid communication with a vacuum conduit 104 connected to a vacuum source (not shown).

The apparatus 96 further comprises a forming chamber 106 through which the forming surface 98 of the drum 100 is movable in a counter-clockwise direction along an arcuate path P generally from an entrance point where forming surface 98 enters the forming chamber substantially free of fibrous material past an exit point where the forming surface exits the forming chamber 106 with a continuous web (108) of absorbent material formed thereon. Absorbent cores 33 are formed by cutting the absorbent web 108 into appropriately sized article lengths (33).

A conventional source of fibrous material, such as a fiber supply reservoir (not shown) or a fiberizer 110 delivers a fluent fibrous material (e.g., a flow of discrete fibers) into the forming chamber 106. The fiberizer 110 shown in FIG. 13 is operatively positioned above the forming chamber 106 and can be a rotary hammer mill or a rotatable picker roll. Suitable fiberizers are available from Paper Converting Machine Company of Green Bay, Wis., U.S.A. The fibrous material may include natural fibers, synthetic fibers and combinations thereof, as previously discussed. The fibrous material employed in the apparatus 96 of FIG. 13 is derived from a batt B of wood pulp cellulose fibers fed to the fiberizer 110 which converts the batt into discrete fibers and delivers fluidized fibrous material into the forming chamber 106.

Other fibrous or particulate material for forming the absorbent web 108 may additionally be delivered into the forming chamber 106. For example, particles or fibers of superabsorbent material may be introduced into the forming chamber 106 by employing conventional mechanisms such as pipes, channels, spreaders, nozzles and the like, as well as combinations thereof. As illustrated, superabsorbent material is delivered into the forming chamber 106 by delivery conduit and nozzle system 112. The fibers, particles and other desired material may be entrained in any suitable fluid medium within the forming chamber, and any reference herein to air forming encompasses other operative techniques. The forming chamber 106 is supported by a suitable support frame (not shown). The forming surface 98 is illustrated as part of the forming drum 100, but other techniques for providing a mat or core forming surface may be employed. For example, the forming surface may be provided by an endless forming belt (not shown) of the type disclosed in U.S. Pat. No. 5,466,409 entitled FORMING BELT FOR THREE-DIMENSIONAL FORMING APPLICATIONS issued on Nov. 14, 1995.

In operation, a vacuum source draws a vacuum through the vacuum duct 102 acting on the interior of the forming surface 98, as it enters and then moves through the forming chamber 106 along a forming path P toward the exit point from the chamber. The fluidized fibrous materials and other particles within the forming chamber are drawn inwardly against the foraminous forming surface 98, and air passes inwardly through the forming surface and out of the drum 100 through the vacuum duct 102 and vacuum supply conduit 104. Fibers and other particulates deposited on the forming surface 98 form the absorbent web 108. Subsequently, the forming surface 98 carrying the absorbent web 108 passes out of the forming chamber 106 through the exit to a scarfing system 114 where the absorbent web 108 can be trimmed and shaped, and excess fibrous material is removed and transported away from the scarfing chamber 114 in a suitable manner known in the art. After the scarfing operation, the portion of the forming surface 98 on which the absorbent web 108 has been formed moves to a release zone where the absorbent web is drawn away from the forming surface 98 onto a transfer station conveyor 118 or other transfer or processing means. The release can be assisted by the application of air pressure from the interior of the drum 100.

As shown in FIG. 13, the conveyor 118 includes an endless perforated conveyor belt 120, and a vacuum suction box 122 is located below the conveyor belt 120 to draw the absorbent web 108 away from the forming surface 98 and onto the belt 120. Removal of the absorbent web 108 can be selectively accomplished by the weight of the absorbent member, by centrifugal force, by mechanical ejection, by positive air pressure or by some other suitable method. The apparatus 96 and method described for air forming a fibrous absorbent member is generally conventional and well known in the art. For example, see U.S. Pat. No. 4,666,647 entitled APPARATUS AND METHOD FOR FORMING A LAID FIBROUS WEB issued May 19, 1987; and U.S. Pat. No. 4,761,258 entitled CONTROLLED FORMATION OF LIGHT AND HEAVY FLUFF ZONES issued Aug. 2, 1988. Other such apparatus are described in U.S. Pat. No. 6,330,735 entitled APPARATUS AND PROCESS FOR FORMING A LAID FIBROUS WEB WITH ENHANCED BASIS WEIGHT CAPABILITY issued Dec. 18, 2001; and U.S. patent application Ser. No. 09/947,128, entitled MULTI-STAGE FORMING DRUM COMMUTATOR filed Sep. 4, 2001. Examples of techniques for introducing a selected quantity of superabsorbent particles into a forming chamber (106) are described in U.S. Pat. No. 4,927,582 entitled METHOD AND APPARATUS FOR CREATING A GRADUATED DISTRIBUTION OF GRANULE MATERIALS IN A FIBER MAT issued May 22, 1990

Still referring to FIG. 13, the forming chamber 106 of the apparatus 96 further comprises a scrim delivery station 123 through which a reinforcing scrim member 40 is introduced into the interior of the forming chamber 106 for incorporation into the absorbent web 108. The scrim 40 is delivered to the forming apparatus 96 in a continuous web and at a predetermined point between the entry and exit points of the forming chamber 106 as a thickness direction control for locating the scrim 40 within the absorbent core 33 being formed. The scrim 40 is sufficiently porous to permit air flowing within the forming chamber 106 to pass through the forming surface 98 as the absorbent core is being deposited thereon, and the mesh openings 86 in the scrim 40 are permeable to the discrete fibers flowing within the forming chamber 106. The force of the vacuum (102) within the drum 100 is believed to provide the impetus for the entanglement action of the fibers with the scrim 40. To form discrete absorbent cores 33 embodying reinforcing scrim members 40, a cutter 124 is positioned downstream from the release zone at the transfer station (122). The cutter 124 cuts the composite web and absorbent core web 108 into discrete article lengths 33 for further processing in making individual absorbent articles 10. The scrim units 40 can also be cut apart upon entry into the forming chamber 106. However, by keeping the scrim 40 (or other reinforcing member) in a unified web during formation of the absorbent core web 108 in the forming chamber 106, the reinforcing member is much easier to handle.

In desired arrangements of absorbent articles, still other features may be employed to improve the strength, integrity, absorbency and comfort of the article. For instance, to improve the containment of the high-absorbency material, the absorbent structure 32 can include an overwrap, such as a wrap sheet 74, which is placed immediately adjacent to and around the absorbent core 33 and may be bonded to the absorbent core and to the various other components of the diaper 10. The wrap sheet 74 encloses substantially all of the peripheral edges of the absorbent core to form a substantially complete envelope thereabout but, alternatively, the wrap sheet 74 can provide an absorbent wrapping covering the major bodyside and outerside surfaces of the absorbent core 33 and only encloses the lateral side edges of the absorbent core. The bodyside and outerside layers of the wrap sheet 74 may be composed of substantially the same material, or may be composed of different materials. For example, the outerside layer of the wrap sheet 74 may be composed of a relatively lower basis weight material having a relatively high porosity, such as a wet strength cellulosic tissue composed of softwood pulp. The bodyside layer of the wrap sheet 74 may have a relatively low porosity to better prevent the migration of superabsorbent particles onto the wearer's skin. In another arrangement, a spacer layer (not shown) may be interposed between the absorbent structure 32 and the backsheet layer 30 to provide desired benefits. Where the backsheet layer 30 is vapor permeable, the spacer layer can separate the backsheet layer 30 away from the absorbent structure 32 to help to reduce a damp or cool feeling that may arise when the absorbent becomes wetted.

In the evolution of improved absorbent articles such as diapers 10, the importance of employing a reinforcing member or scrim 40 for the absorbent core 33 has become evident. In a series of direct comparative tests of diaper structures having a scrim reinforcement with similar structures without such reinforcement these diaper structures were evaluated to determine the following:

good integrity and intact core;
binding and clumping;
core splitting, (front and/or back);
total core disintegration.

Such testing was conducted during daytime "play" conditions and during inactive nighttime conditions. The results of such testing indicates that scrim reinforced absorbent core out performs conventional, unreinforced diapers because it eliminates or substantially reduces the bunching, clumping, splitting and disintegration thereof in normal use conditions. Thus, the incorporation of a scrim reinforcement material internally into the absorbent core structure greatly reduces the lack of integrity problems associated with unreinforced diaper structures. However, in some cases scrim reinforcement has been found to result in undesirable absorbent core stiffness which may cause skin irritation or otherwise adversely impact on conformability, fit and comfort especially in the crotch region of the articles. The present invention is directed to overcoming these shortcomings.

Referring now to FIGS. 4-11, different embodiments of the reinforcing scrim member (40, 140, 240, 340, 440, 540, 640, 740, and 840) are illustrated as examples of carrying out the present invention. In conventional scrim 40 (FIG. 3), the MD strands 82 and CD strands 84 are typically formed of the same selected material and are the same size (e.g., diameter and/or thickness) and weight. These strands 82, 84 are arranged in an evenly spaced, perpendicular or crossing relationship to form the open lattice-work mesh (or network) with square openings 86 through which the fibers of the core 33 can pass and become entwined, as previously discussed. In other words, in the conventional FIG. 3 form of scrim 40, there is a uniform spacing between the elongate MD strands 82 and the same spacing between the CD strands so that a square grid or web 40 is formed by this co-relationship in the frequency of MD and CD strands in both directions. In each of the different embodiments herein, there is at least one significant characteristic difference between the MD strands and the CD strands to thereby achieve an increased edge load yieldability (characterized primarily by a diminished resistance to buckling) in the CD direction 26. This results in less CD strand stiffness and reduces irritation and discomfort to the wearer of the diaper 10.

Figure 4:
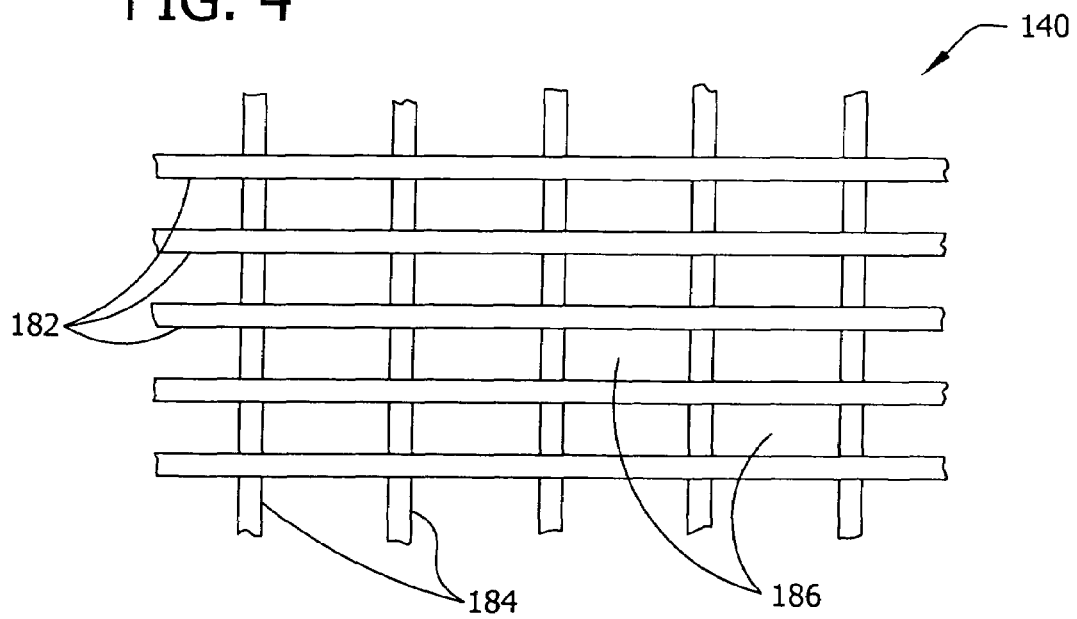
FIG. 4 is an enlarged, fragmentary plan view of a first reinforcement member embodiment of the invention.

Referring to FIGS. 2A and 4, one aspect of the invention is to reduce the frequency of the CD strands 184 relative to the occurrence of the MD strands 182 in scrim web 140 to thereby reduce cross-directional (26) absorbent core stiffness. The ratio of the number of cross direction CD strands 184 to machine direction MD strands 182 is less than 1:1, or about 1:2 (50%) per unit area or in a range from about 50% to 90%. The predetermined frequency (spacing) of the MD strands 182 achieves optimum strength of absorbent core reinforcement in the elongate machine direction 24 of the diaper 10, and the reduced frequency of the CD strands 184 supports the MD strand action while permitting or facilitating a lateral cross direction yielding of the scrim web 140 to provide reduced stiffness in the CD direction 26. Thus, in FIG. 4 it will be seen that the openings 186 are rectangular, being elongated in the machine direction 24.

Figure 5:
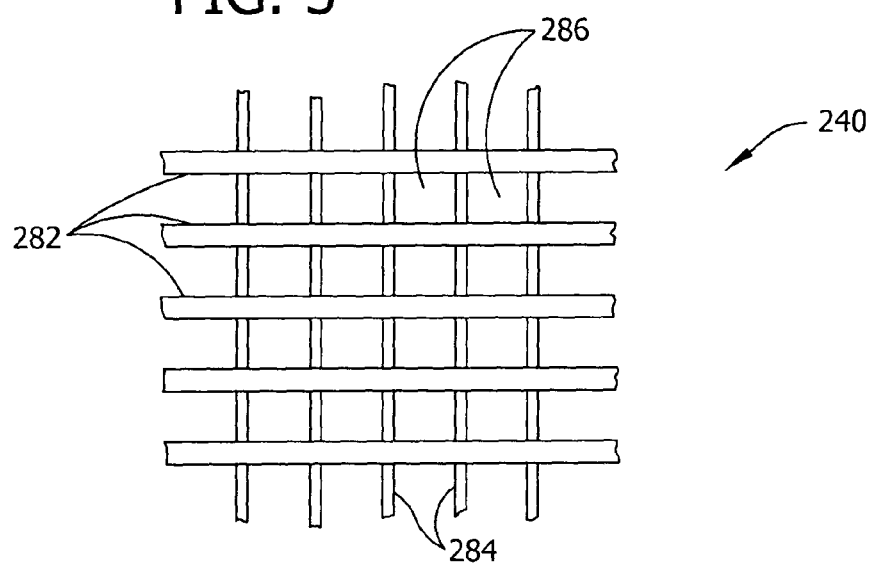
FIG. 5 is a view similar to FIG. 4 of a second reinforcement member embodiment.

Referring to FIGS. 2B and 5, another aspect of the invention is to reduce the relative stiffness of the scrim web 240 in the cross direction 26 of the CD strands 284 relative to the action of the MD strands 282. In this embodiment, the diameter of at least some of the CD strands 284 is reduced relative to the diameter of the MD strands in the scrim 240. Such reduced diameter requires less force to bend, buckle or deform. It is within the scope of this embodiment teaching to selectively control the denier or sizing of both CD and MD strands to achieve optimum strength of the scrim 240 in the machine direction while providing an increased flexibility of the scrim in the cross direction. It may be noted (based on Euler's column buckling formula) that the buckling strength of a substantially circular scrim strand is proportional to its radius raised to the 4th power, which means that a relatively small decrease in strand diameter will have a large impact on reducing its strength against buckling. In the embodiment shown in FIGS. 2A and 5, all of the CD strands 284 have a smaller diameter than the diameter of the MD strands 282, and the ratio of the size of CD strand diameter to MD strand diameter is about 1:2 (50% or less). The ratio of CD strand to MD strand diameter is less than 1:1 and in range extending to less than 50%. It may be noted that according to Euler's column buckling formula, a CD strand diameter of about 93% of MD strand size will result in a 25% reduction in cross direction buckling strength, and a 50% reduction in buckling strength can be achieved if the CD strand diameter is reduced to 83% of the MD strand diameter.

Figure 6A:
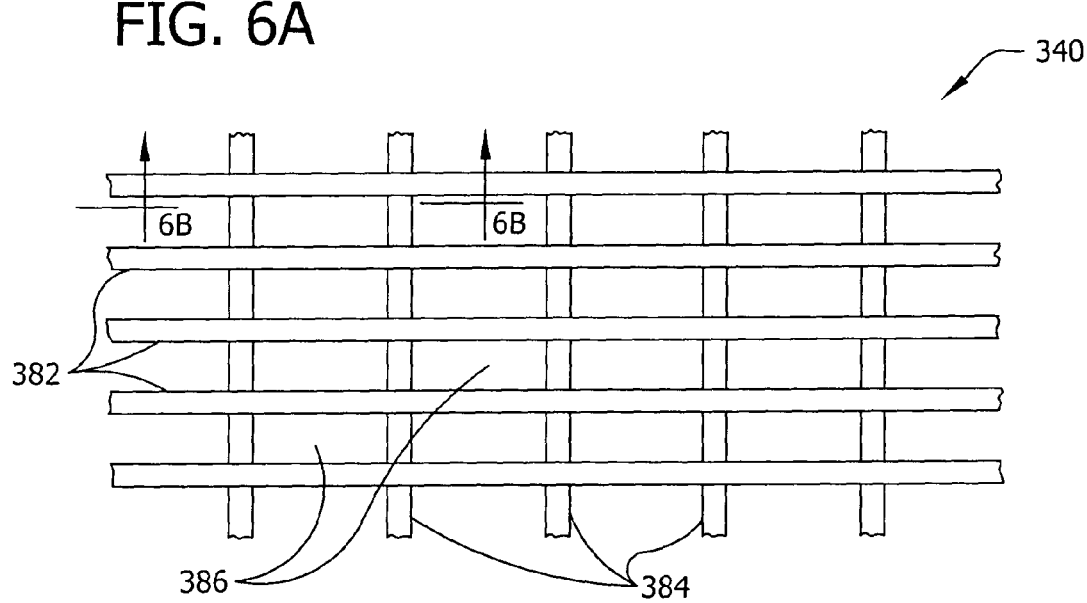
FIG. 6A is a view similar to FIG. 4A of a third reinforcement member embodiment.
Figure 6B:
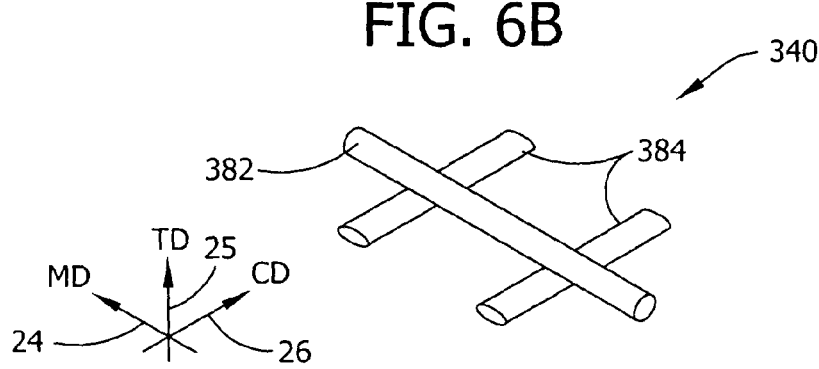
FIG. 6B is a cross-sectional view taken on line 6B-6B of FIG. 6A.

Referring to FIGS. 6A and 6B, in another aspect of the invention, the profile of the CD strand 384 can be changed to increase or maintain relative machine direction strength while facilitating cross direction buckling or folding of the CD strands 384. In this embodiment the MD strands 382 may be circular in cross section and of preselected diameter and/or TD direction thickness to achieve optimum machine direction strength. The CD strands 384 may be generally elliptical as shown in FIG. 6B, having a major axis that extends in the machine direction and a minor axis that extends in a thickness direction TD. The ratio of the minor axis of the CD strands 384 to the diameter of the MD strands 382 is below 1:1, and generally in the range of 93% to 50% or less, as discussed with reference to FIG. 5. The minor axis orientation allows the CD strands 384 to more readily bend or buckle about the major axis, which reduces cross directional stiffness. One advantage of this construction is that CD strands 384 can be formed initially the same as MD strands 382 and then flattened (or otherwise formed) into a generally elliptical shape. In practice, neither the MD strands 382 nor the CD strands 384 will be perfectly round or elliptical. The MD strands 382 may also be generally elliptical. In that case, the dimensions of the minor axes of the elliptical CD strands will on average be less than dimensions of the minor axes of the MD strands.

Figure 7A:
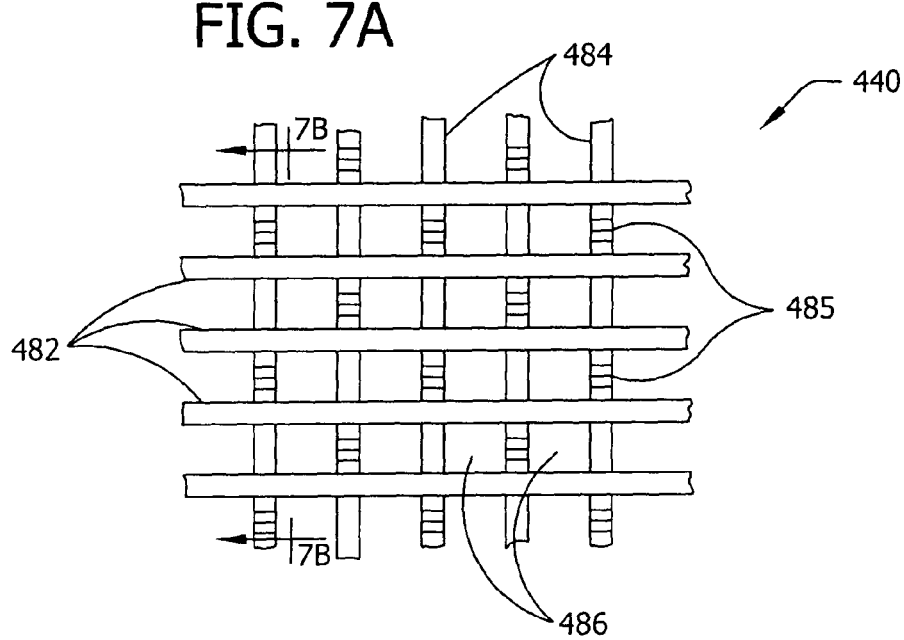
FIG. 7A is a fourth reinforcement member embodiment.
Figure 7B:
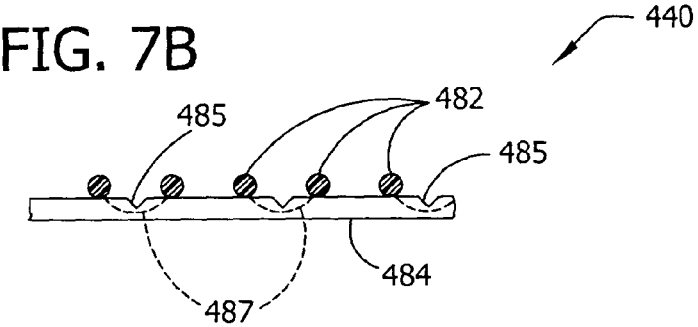
FIG. 7B is a cross-sectional view taken substantially on line 7B-7B of FIG. 7A.
Figure 8:
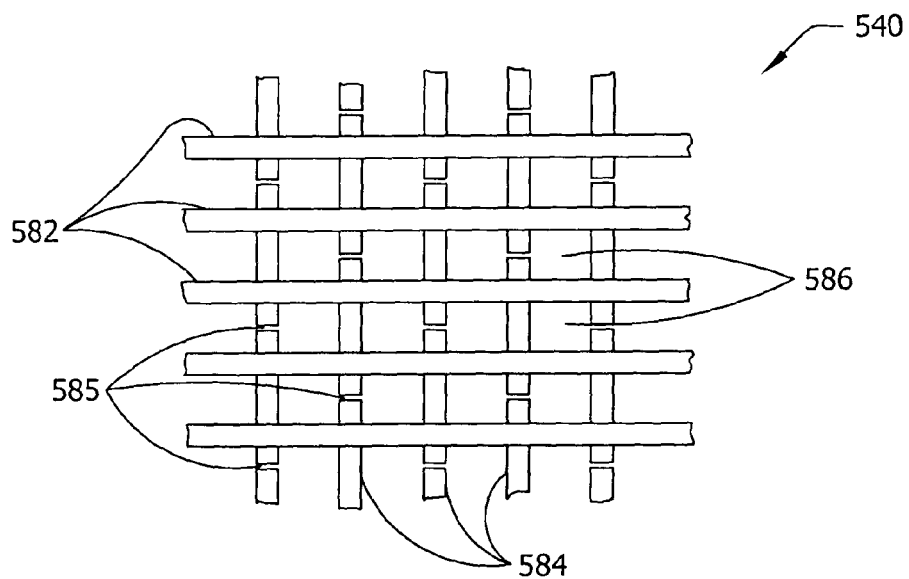
FIG. 8 is a fifth reinforcement member embodiment.

In other embodiments shown in FIGS. 7A, 7B and 8, the scrim webs 440, 540 can have the CD strands 484, 584 mechanically, hydraulically, ultrasonically, or thermally scored, abraded, degraded, compressed, cut or otherwise modified at selected points or areas along the cross directional length to create controlled buckling points to thereby increase flexibility and reduce stiffness. As shown in FIGS. 7A and 7B, the CD strands 484 can be notched or abraded, at 485, to have reduced dimension in the thickness direction TD at preselected points. As shown, this notching 485 can be carried out on selected CD strand segments as between alternate spaced apart pairs of MD strands 482 so that a notched segment (485) occurs between every other adjacent pair of MD strands 482. Clearly this frequency of notches 485 along the CD strands 484 can be varied, and the linear location of such notches 485 on successive CD strands can be arranged at offset or staggered locations on consecutive CD strands. Clearly, notches 485 can be constructed, formed and arranged in different selective patterns to achieve optimum CD strand flexibility while maintaining the structural integrity of the absorbent core 33 in both the machine direction and the cross direction of the scrim web 440. In a similar manner illustrated in FIG. 7B, instead of notches 485 the CD strands 484 can be abraded or compressed (as at 487) to provide weakened preselected areas. FIG. 8 shows another embodiment in which the CD strands 584 can be selectively cut, at 585, at predetermined spaced locations on successive or spaced CD strands to achieve cross directional yieldability.

Figure 9A:
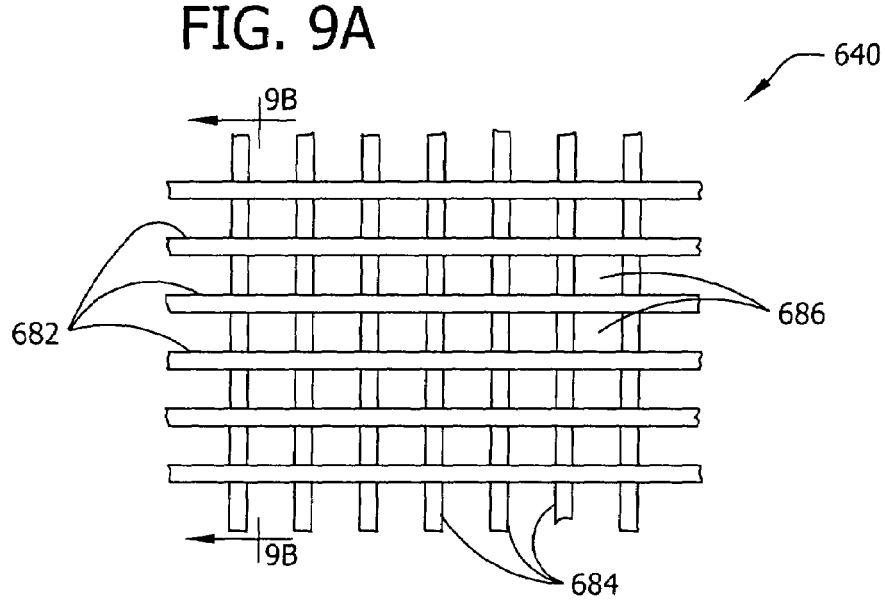
FIG. 9A is a sixth reinforcement member embodiment.
Figure 9B:
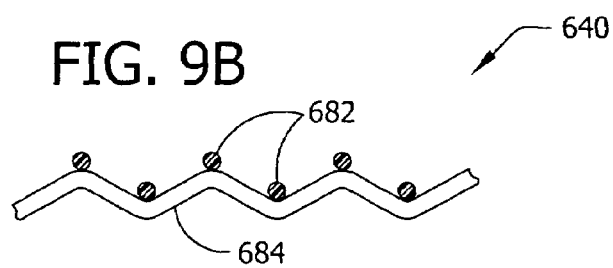
FIG. 9B is a cross-sectional view taken substantially on line 9B-9B of FIG. 9A.

Referring to FIGS. 9A and 9B, in an alternate form of the invention the CD strands 684 are corrugated, as in a creased accordion-type fold, and the MD strands 682 are arranged at alternating thickness direction levels to connect with the peaks and valleys of the CD strands 684. The CD strands 684 need not be smaller in size than the MD strands 682 to still achieve a high degree of yieldability. The folds allow the scrim to give way in the cross direction by folding even more so that the peaks and valleys are closer together.

Figure 10:
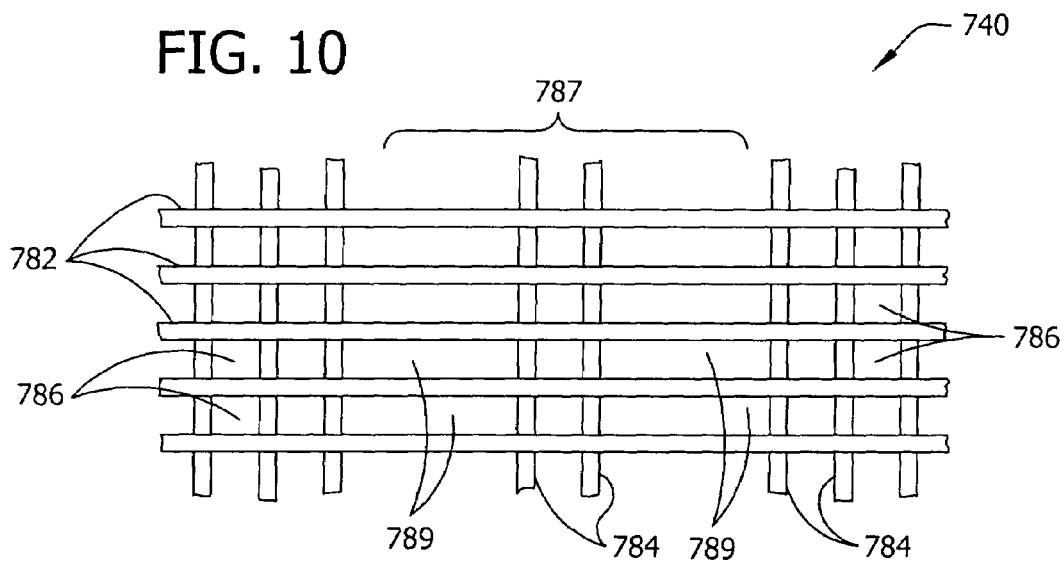
FIG. 10 is a seventh reinforcement member embodiment.

In still another embodiment shown in FIG. 2C and 10, the MD strands 782 of a ribbon of scrim web 740 are constructed with a selected diameter and shape, and arranged in a substantially uniformly spaced pattern. The transversely crossing CD strands 784 are arranged in spaced groups of two or more CD strands to achieve at least one predetermined control zone 787 for providing strategic yieldability. Thus, a single control zone 787 may be located along the line of the MD strands 782 to form a more pliable crotch area of the diaper 10. In FIG. 10 for example, the controlled zone 787 has a pair of centrally located CD strands 784 widely spaced from end portions of the scrim 740 in which more conventional CD strand spacing is provided. Thus this scrim pattern provides relatively long rectangular mesh openings 789 in the MD direction on both sides of the central control zone part of CD strands whereas the respective end portions of the scrim 740 may have smaller mesh openings 786.

Figure 11:
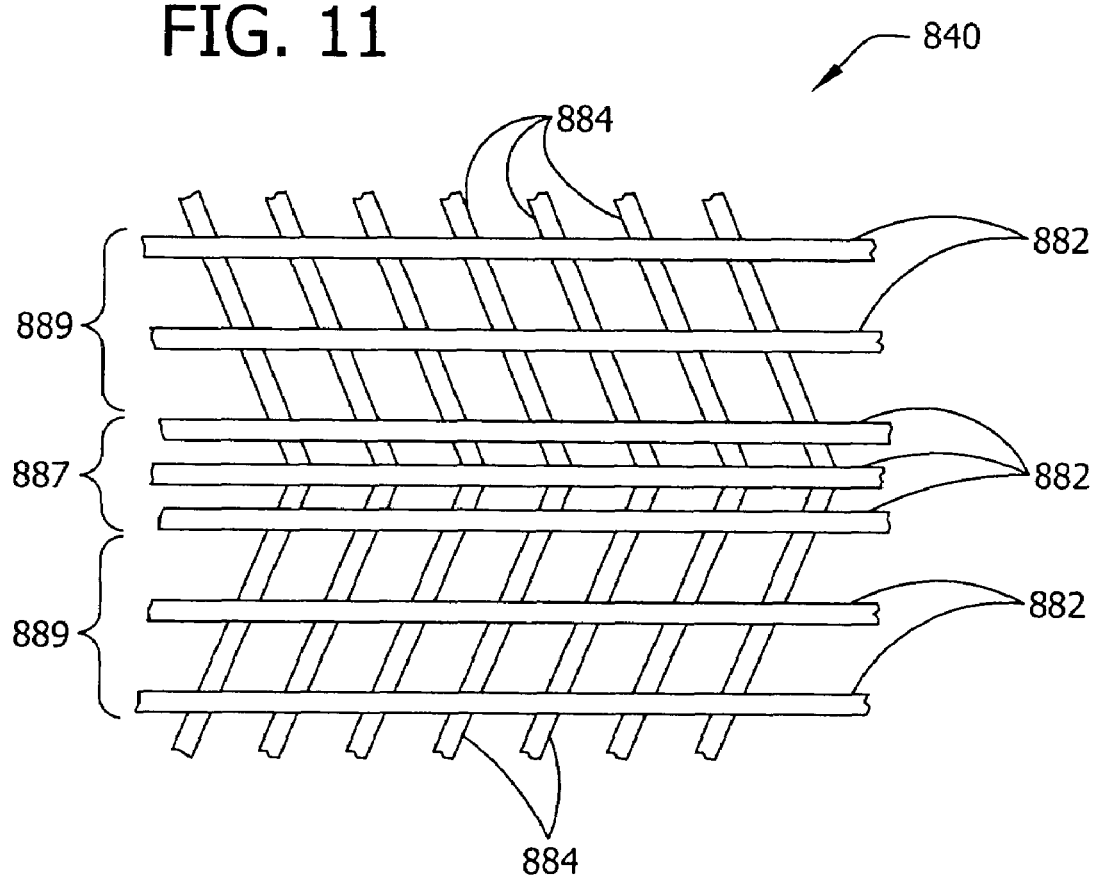
FIG. 11 is an eighth reinforcement member embodiment.

Referring to FIG. 11 in another embodiment of the invention the scrim 840 is constructed with a central elongated zone 887 in which the frequency of MD strands 882 is increased relative to frequency of parallel side zones 889 of the scrim 840. This provides a preselected strength of the scrim 840 in the MD direction within the central "anchor" zone 887 while permitting greater yieldability in the design selections for the side zones 889. In this embodiment the CD strands 884 are shown arranged to extend from the central zone 887 at diverging angles from each other and non-orthogonal to the MD strands 882. Such angularity enhances the yieldability of the side zones (889) relative to the central zone (887) of the scrim 840.

Figure 12A:
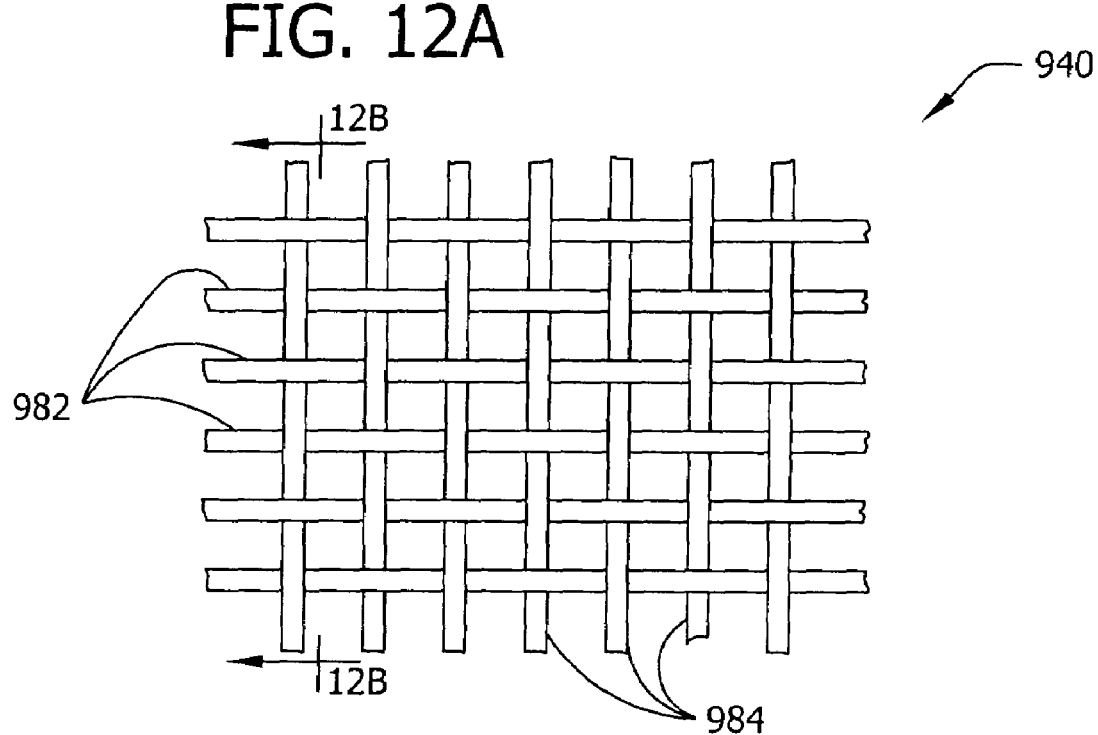
FIG. 12A is a ninth reinforcement member embodiment.
Figure 12B:
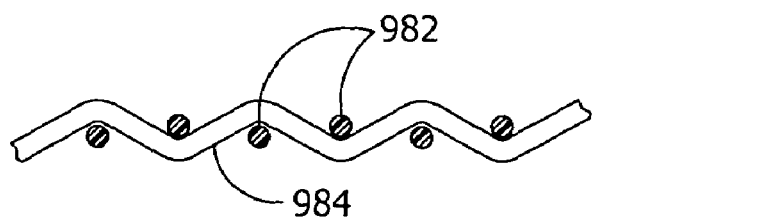
FIG. 12B is a cross-sectional view taken substantially on line 12B-12B of FIG. 12A.

A ninth embodiment of the invention shown in FIGS. 12A and 12B comprises scrim 940 having MD strands 982 which are generally co-planar, and CD strands 984 which are woven under and over the MD strands. As best seen in FIG. 12B, the weaving of the CD strands so that they pass above one MD strand and below the next MD strand introduces bends or kinks in the CD strands. The terms "under" and "over" and "above" and "below" are used for convenience of description in relation to the orientation shown in the drawings, but do not require any absolute orientation of the scrim or its component parts. These kinks facilitate bending of the CD strands under application of a transverse force so that the scrim 940 is relatively more yieldable in the CD direction than in the MD direction. The kinks cause the CD strands to experience these transverse forces more in bending (which is resisted relatively weakly) than in compression (which is resisted strongly). Other arrangements (not shown) are envisioned, such as both the MD strands and the CD strands being woven.

In another embodiment of the invention for reducing stiffness of a reinforcing scrim member 40 (140, 240, 340, 440, 540, 640, 740, 840, 940) or the like, the scrim material composition can be modified or changed to use a lower modulus of elasticity raw material in the CD strands 84 (184-984). Lower modulus of elasticity materials can include inherently more flexible, extensible, elastic or bicomponent natural or synthetic materials. Suitable polymers, co-polymers or blends for the scrim matrix include thermoplastic resins, elastomeric co-polymers, polyolefins (i.e. polypropylene, polyethylene), polyesters, polyurethanes and latex formulations. Examples of specific polymers include poly (ethylene-vinylacete, EVA), poly (styrene-butadiene), poly (styrene-acrylic), vinyl acrylic terpolymer, neoprene, polyester latexes, polyacrylates and nylon. These can be non-crosslinking or, in some cases, crosslinking.

It is also possible to achieve a relative weakness of the CD strands relative to the MD strands of substantially the same material by introduction of a weakening additive to the CD strands. For instance by adding calcium carbonate to the CD strands, voids are formed in the strands which produce weakened points where bending and buckling may occur. It is unnecessary for the CD strands to be otherwise different from the MD strands. For example, both the MD strands and CD strands may be made of polypropylene, but with the CD strands further containing a calcium carbonate or other suitable additive which weakens the CD strands relative to the MD strands.

When introducing elements of the present invention or the various embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article for absorbing body fluids comprising an absorbent core being at least partially made of fibers and constructed and arranged for receiving and holding such fluids and including a reinforcing scrim member intimately associated with the absorbent core to maintain its structural integrity in use, the absorbent core having an upper region and a lower region, the scrim member being located intermediate the upper and lower regions, said scrim member comprising a network of machine direction (MD) strands extending in a machine direction, and cross direction (CD) strands extending in a cross direction, at least some of said MD strands and CD strands crossing over each other and being interconnected, the MD strands and the CD strands cooperatively defining a plurality of openings in the scrim member, said MD strands being selected and formed to provide a predetermined stiffness and strength in supporting said absorbent core in the machine direction, and said CD strands being selected and formed with at least one characteristic difference from said MD strands to provide a stiffness of the absorbent core in the cross direction that is less than said stiffness of the absorbent core in the machine direction, wherein the network of MD strands and CD strands is formed with at least some of the CD strands being continuous and having weakened points along their lengths to enhance buckling, the scrim member being attached to the absorbent core through at least one of fibers from the upper region of the absorbent core passing through openings in the scrim member and entangling with fibers from the lower region; fibers from the lower region of the absorbent core passing through the openings in the scrim member and entangling with fibers in the upper region; fibers from the upper region of the absorbent core passing through openings in the scrim member and entangling with other fibers in the upper region so that the entangled fibers encircle and thereby capture at least one strand of the scrim member; and fibers from the lower region of the absorbent core passing through openings in the scrim member and entangling with other fibers in the lower region so that the entangled fibers encircle and thereby capture at least one strand of the scrim member, wherein the CD strands are at least one of notched, abraded and compressed at predetermined places between preselected MD strands to provide the weakened points.

2. The absorbent article as set forth in claim 1, wherein the weakened points on one of the CD strands are offset in the cross direction from the weakened points on an adjacent CD strand.

3. The absorbent article as set forth in claim 1, wherein the weakened points are reduced in at least one transverse dimension of the CD strands as compared to other parts of the CD strands.

4. The absorbent article as set forth in claim 1 wherein the absorbent article is a disposable garment.

5. The absorbent article as set forth in claim 4 wherein the absorbent article is a diaper.

6. The absorbent article as set forth in claim 4 wherein the absorbent article is a child's training pants.

7. The absorbent article as set forth in claim 4 wherein the absorbent article is one of an adult incontinence diaper, adult incontinence pad, adult incontinence pant and adult incontinence undergarment.

8. An absorbent article for absorbing body fluids comprising an absorbent core constructed and arranged for receiving and holding such fluids and including a reinforcing scrim member intimately associated with the absorbent core to maintain its structural integrity in use, said scrim member comprising a network of machine direction (MD) strands extending in a machine direction, and cross direction (CD) strands extending in a cross direction, at least some of said MD strands and CD strands crossing over each other and being interconnected, said MD strands being selected and formed to provide a predetermined stiffness and strength in supporting said absorbent core in the machine direction, and said CD strands being selected and formed with at least one characteristic difference from said MD strands to provide a stiffness of the absorbent core in the cross direction that is less than said stiffness of the absorbent core in the machine direction, wherein the network of MD strands and CD strands is formed with at least some of the CD strands having weakened points along their lengths to enhance buckling, the CD strands being at least one of notched, abraded and compressed at predetermined places between preselected ones of the MD strands to provide the weakened points, and wherein the weakened points on the CD strands are cut through, and such weakened points on one CD strand are offset from the weakened points on an adjacent CD strand.

9. The absorbent article as set forth in claim 8, wherein the scrim member is attached to the absorbent core through entanglement of at least some fibers of the absorbent core with the CD strands of the scrim member and at least some other fibers of the absorbent core with the MD strands of the scrim member.

10. The absorbent article as set forth in claim 8 wherein the CD strand is corrugated and forms peaks and valleys along the cross direction thereof, said MD strands being arranged to engage the CD strands across the peaks and valleys thereof.

11. The absorbent article as set forth in claim 8 wherein the CD strands are woven under and over the MD strands.

12. The absorbent article as set forth in claim 8, wherein at least some of said CD strands are generally elliptical in cross-section and have major and minor axes, the minor axis being arranged substantially normal to a plane of the MD strands.

13. The absorbent article as set forth in claim 12 wherein the MD strands are generally elliptical in cross-section, having major and minor axes, the minor axes of the CD strands being on average of a lesser dimension than the minor axes of the MD strands.

14. The absorbent article as set forth in claim 8 wherein the MD strands are spaced according to a first spacing frequency, and at least some of said CD strands have a second spacing frequency different from the first spacing frequency of the MD strands.

15. The absorbent article as set forth in claim 14, wherein the machine direction of the scrim member has end zones and a central zone, and said second spacing frequency of CD strands being provided in said central zone.

16. The absorbent article as set forth in claim 14, wherein a ratio of the second spacing frequency of CD strands to the first spacing frequency of MD strands is about 0.9 (CD) to 1.0 (MD).

17. The absorbent article as set forth in claim 16 wherein the ratio is about 0.75 (CD) to 1.0 (MD).

18. The absorbent article as set forth in claim 16, wherein the ratio is about 0.5 (CD) to 1.0 (MD).

19. The absorbent article according to claim 16, wherein the reduced frequency range of CD strands is about 0.9 to 0.5 relative to the frequency of MD strands at 1.0.

20. The absorbent article as set forth in claim 8 wherein said MD strands each have a strand diameter, and wherein said CD strands each have a strand diameter less than said MD strand diameter.

21. The absorbent article as set forth in claim 20 wherein both of said MD strands and said CD strands are round in cross-section.

22. The absorbent article as set forth in claim 20, wherein a strand diameter ratio of the CD strand diameter to the MD strand diameter is less than about 0.95.

23. The absorbent article as set forth in claim 22, wherein the strand diameter ratio is less than about 0.9.

24. The absorbent article as set forth in claim 23, wherein the strand diameter ratio is less than about 0.75.

25. The absorbent article as set forth in claim 24, wherein the strand diameter ratio is less than about 0.5.

* * * * *